(12) United States Patent
Pavlovic et al.

(10) Patent No.: US 9,504,840 B2
(45) Date of Patent: Nov. 29, 2016

(54) METHOD OF FORMING A CERMET-CONTAINING BUSHING FOR AN IMPLANTABLE MEDICAL DEVICE HAVING A CONNECTING LAYER

(71) Applicant: Heraeus Precious Metals GmbH & Co. KG, Hanau (DE)

(72) Inventors: Goran Pavlovic, Schaafheim (DE); Jeremy Glynn, Buffalo, MN (US)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 78 days.

(21) Appl. No.: 14/593,637

(22) Filed: Jan. 9, 2015

(65) Prior Publication Data

US 2015/0122875 A1  May 7, 2015

Related U.S. Application Data

(62) Division of application No. 13/361,362, filed on Jan. 30, 2012, now abandoned.

(60) Provisional application No. 61/438,033, filed on Jan. 31, 2011.

(30) Foreign Application Priority Data

Jan. 31, 2011  (DE) .......... 10 2011 009 858

(51) Int. Cl.
*A61N 1/375* (2006.01)
*B23K 1/00* (2006.01)

(52) U.S. Cl.
CPC ........... *A61N 1/3752* (2013.01); *A61N 1/3754* (2013.01); *B23K 1/0016* (2013.01); *B23K 2001/12* (2013.01); *Y10T 29/49227* (2015.01)

(58) Field of Classification Search
None
See application file for complete search history.

(56) References Cited

U.S. PATENT DOCUMENTS 3,025,441 A  3/1962 West
3,063,144 A  11/1962 Palmour, III
(Continued)

FOREIGN PATENT DOCUMENTS

CN  87210627  6/1988
CN  1452232  10/2003
(Continued)

OTHER PUBLICATIONS

The Office Action for U.S. Appl. No. 13/361,340 mailed Mar. 12, 2015 (23 pages).
(Continued)

*Primary Examiner* — Devang R Patel
(74) *Attorney, Agent, or Firm* — Dicke, Billig & Czaja, PLLC (57) ABSTRACT

One aspect relates method of forming an electrical bushing for an implantable medical device, including generating at least one base body green compact for at least one base body from an insulating composition of materials. At least one cermet-containing conducting element green compact is formed for at least one conducting element. At least one conducting element green compact is introduced into the base body green compact. The insulation element green compact is connected to the at least one base body green compact in order to obtain at least one base body having at least one conducting element. A connecting layer is applied onto the at least one conducting element.

17 Claims, 3 Drawing Sheets

(56) References Cited

U.S. PATENT DOCUMENTS

| | | |
|---|---|---|
| 3,646,405 A | 2/1972 | Wallis et al. |
| 3,979,187 A | 9/1976 | Scherer |
| 4,152,540 A | 5/1979 | Duncan et al. |
| 4,159,075 A | 6/1979 | Ljung et al. |
| 4,217,137 A | 8/1980 | Kraska et al. |
| 4,225,262 A | 9/1980 | Koop et al. |
| 4,315,054 A | 2/1982 | Sack et al. |
| 4,354,964 A | 10/1982 | Hing et al. |
| 4,488,673 A | 12/1984 | Hopper, Jr. |
| 4,602,956 A | 7/1986 | Partlow et al. |
| 4,678,868 A | 7/1987 | Kraska et al. |
| 4,991,582 A | 2/1991 | Byers et al. |
| 5,043,535 A | 8/1991 | Lin |
| 5,515,604 A | 5/1996 | Horine et al. |
| 5,601,638 A | 2/1997 | Fukuda et al. |
| 5,735,884 A | 4/1998 | Thompson et al. |
| 5,738,270 A | 4/1998 | Malmgren |
| 5,769,874 A | 6/1998 | Dahlberg |
| 5,796,019 A | 8/1998 | Lupton et al. |
| 5,861,714 A | 1/1999 | Wei et al. |
| 5,870,272 A | 2/1999 | Seifried et al. |
| 6,093,476 A | 7/2000 | Horiuchi et al. |
| 6,414,835 B1 | 7/2002 | Wolf et al. |
| 6,643,903 B2 | 11/2003 | Stevenson et al. |
| 6,660,116 B2 | 12/2003 | Wolf et al. |
| 6,841,731 B1 | 1/2005 | Zanello |
| 6,999,818 B2 | 2/2006 | Stevenson et al. |
| 7,035,076 B1 | 4/2006 | Stevenson |
| 7,038,900 B2 | 5/2006 | Stevenson et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,211,103 B2 | 5/2007 | Greenberg |
| 7,260,434 B1 | 8/2007 | Lim et al. |
| 7,274,963 B2 | 9/2007 | Spadgenske |
| 7,341,802 B1 | 3/2008 | Ota et al. |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,630,768 B1 | 12/2009 | Coffed et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,163,397 B2 | 4/2012 | Ok et al. |
| 8,179,658 B2 | 5/2012 | Brendel et al. |
| 8,288,654 B2 | 10/2012 | Taylor et al. |
| 8,289,105 B2 | 10/2012 | Chereson et al. |
| 8,326,425 B2 | 12/2012 | Sprain et al. |
| 8,346,362 B2 | 1/2013 | Kinney et al. |
| 8,355,785 B1 | 1/2013 | Hammond et al. |
| 8,378,239 B2 | 2/2013 | Lakner et al. |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,538,530 B1 | 9/2013 | Orinski |
| 8,552,311 B2 | 10/2013 | Koester et al. |
| 8,626,310 B2 | 1/2014 | Barror et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,825,162 B2 | 9/2014 | Reisinger |
| 8,894,914 B2 | 11/2014 | Pavlovic |
| 9,032,614 B2 | 5/2015 | Specht |
| 9,040,819 B2 | 5/2015 | Kempf et al. |
| 9,048,608 B2 | 6/2015 | Pavlovic |
| 9,088,093 B2 | 7/2015 | Reisinger et al. |
| 9,126,053 B2 | 9/2015 | Kempf et al. |
| 9,306,318 B2 | 4/2016 | Reisinger |
| 2001/0013756 A1 | 8/2001 | Mori et al. |
| 2004/0116976 A1 | 6/2004 | Spadgenske |
| 2004/0128016 A1 | 7/2004 | Stewart |
| 2006/0247714 A1 | 11/2006 | Taylor et al. |
| 2006/0259093 A1 | 11/2006 | Stevenson et al. |
| 2007/0183118 A1 | 8/2007 | Fu et al. |
| 2008/0060834 A1 | 3/2008 | Eck et al. |
| 2008/0060844 A1 | 3/2008 | Teske et al. |
| 2008/0119906 A1 | 5/2008 | Starke |
| 2008/0203917 A1 | 8/2008 | Maya |
| 2008/0269831 A1 | 10/2008 | Erickson |
| 2008/0314502 A1 | 12/2008 | Ok et al. |
| 2009/0192578 A1 | 7/2009 | Biggs |
| 2009/0281586 A1 | 11/2009 | Lim |
| 2010/0023086 A1 | 1/2010 | Lim |
| 2010/0109966 A1 | 5/2010 | Mateychuk et al. |
| 2010/0258342 A1 | 10/2010 | Parker |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0186349 A1 | 8/2011 | Troetzschel et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2014/0262494 A1 | 9/2014 | Reisinger et al. |
| 2014/0368298 A1 | 12/2014 | Reisinger |
| 2015/0270025 A1 | 9/2015 | Specht et al. |

FOREIGN PATENT DOCUMENTS

| | | |
|---|---|---|
| CN | 1658803 | 8/2005 |
| DE | 69729719 | 7/2005 |
| DE | 102006054249 | 5/2008 |
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| EP | 0877400 | 11/1998 |
| EP | 1685874 | 8/2006 |
| EP | 1754511 | 2/2007 |
| WO | 03073450 | 9/2003 |
| WO | 03077781 | 9/2003 |
| WO | 2004110555 | 12/2004 |
| WO | 2008103166 | 8/2008 |
| WO | 2010091435 | 8/2010 |

OTHER PUBLICATIONS

The Notice of Allowance for U.S. Appl. No. 14/293,596 mailed Mar. 17, 2015 (28 pages).

The Notice of Allowance for U.S. Appl. No. 13/361,370 mailed May 1, 2015 (17 pages).

The Office Action for U.S. Appl. No. 13/361,374 mailed May 18, 2015 (12 pages).

(56) References Cited

OTHER PUBLICATIONS

The Restriction Requirement for U.S. Appl. No. 13/361,322 mailed Nov. 14, 2013 (7 pages).
The Office Action for U.S. Appl. No. 13/361,322 mailed Feb. 19, 2014 (26 pages).
The Office Action for U.S. Appl. No. 13/361,340 mailed Oct. 25, 2013 (20 pages).
The Office Action for U.S. Appl. No. 13/361,340 mailed Apr. 29, 2014 (18 pages).
The Restriction Requirement for U.S. Appl. No. 13/361,348 mailed Nov. 14, 2013 (7 pages).
The Office Action for U.S. Appl. No. 13/361,348 mailed Feb. 19, 2014 (23 pages).
The Office Action for U.S. Appl. No. 13/361,355 mailed date Aug. 7, 2013 (21 pages).
The Notice of Allowance for U.S. Appl. No. 13/361,355 mailed Jan. 16, 2014 (18 pages).
The Restriction Requirement for U.S. Appl. No. 13/361,362 mailed Nov. 14, 2013 (7 pages).
The Office Action for U.S. Appl. No. 13/361,362 mailed Feb. 19, 2014 (19 pages).
The Office Action for U.S. Appl. No. 13/361,370 mailed Oct. 29, 2013 (26 pages).
The Office Action for U.S. Appl. No. 13/361,370 mailed May 14, 2014 (18 pages).
The Restriction Requirement for U.S. Appl. No. 13/361,374 mailed Mar. 5, 2013 (6 pages).
The Office Action for U.S. Appl. No. 13/361,374 mailed Oct. 4, 2013 (22 pages).
The Office Action for U.S. Appl. No. 13/361,374 mailed May 1, 2014 (20 pages).
The Restriction Requirement for U.S. Appl. No. 13/361,383 mailed Feb. 27, 2013 (6 pages).
The Office Action for U.S. Appl. No. 13/361,383 mailed Nov. 13, 2013 (22 pages).
The Notice of Allowance for U.S. Appl. No. 13/361,383 mailed Apr. 25, 2014 (18 pages).
The Office Action for U.S. Appl. No. 13/361,388 mailed Feb. 11, 2014 (24 pages).
The Office Action for U.S. Appl. No. 13/361,398 mailed Mar. 7, 2014 (26 pages).
The Restriction Requirement for U.S. Appl. No. 13/361,404 mailed Apr. 8, 2013 (6 pages).
The Restriction Requirement for U.S. Appl. No. 13/361,404 mailed Oct. 9, 2013 (5 pages).
The Office Action for U.S. Appl. No. 13/361,404 mailed Feb. 27, 2014 (19 pages).
The Restriction Requirement for U.S. Appl. No. 13/361,411 mailed Mar. 10, 2014 (7 pages).
The Final Office Action for U.S. Appl. No. 13/361,322 mailed Sep. 9, 2014 (17 pages).
The Final Office Action for U.S. Appl. No. 13/361,340 mailed Oct. 30, 2014 (21 pages).
The Final Office Action for U.S. Appl. No. 13/361,348 mailed Sep. 9, 2014 (19 pages).
The Final Office Action for U.S. Appl. No. 13/361,362 mailed Sep. 9, 2014 (19 pages).
The Final Office Action for U.S. Appl. No. 13/361,370 mailed Nov. 5, 2014 (19 pages).
The Final Office Action for U.S. Appl. No. 13/361,374 mailed Nov. 10, 2014 (19 pages).
The Final Office Action for U.S. Appl. No. 13/361,388 mailed Jul. 31, 2014 (32 pages).
The Notice of Allowance for U.S. Appl. No. 13/361,398 mailed Jul. 25, 2014 (11 pages).
The Final Office Action for U.S. Appl. No. 13/361,404 mailed Oct. 9, 2014 (12 pages).
The Office Action for U.S. Appl. No. 13/361,411 mailed Aug. 1, 2014 (18 pages).
The Office Action for U.S. Appl. No. 13/361,322 mailed Feb. 4, 2015 (19 pages).
The Notice of Allowance for U.S. Appl. No. 13/361,348 mailed Jan. 22, 2015 (9 pages).
The Notice of Allowance for U.S. Appl. No. 13/361,404 mailed Jan. 28, 2015 (6 pages).
The Notice of Allowance for U.S. Appl. No. 13/361,411 mailed Jan. 20, 2015 (8 pages).
The Office Action for U.S. Appl. No. 13/361,388 mailed Feb. 9, 2015 (29 pages).
Hussain, et al., "Electrical conductivity of an insulator matrix (alumina) and conductor particle (molybdenum) composites", Journal of the European Ceramic Society, vol. 23, Issue 2, Feb. 2003, pp. 315-321.
Final Office Action for U.S. Appl. No. 13/361,322 mailed Aug. 24, 2015 (21 pages).
The Restriction Requirement for U.S. Appl. No. 14/729,560 mailed Dec. 22, 2015 (6 pages).
The Restriction Requirement for U.S. Appl. No. 14/729,560 mailed Feb. 22, 2016 (7 pages).
The Final Office Action for U.S. Appl. No. 13/361,340 mailed Nov. 24, 2015 (27 pages).
The Advisory Action for U.S. Appl. No. 13/361,340 mailed Feb. 22, 2016 (4 pages).
The Notice of Allowance for U.S. Appl. No. 13/361,374 mailed Dec. 3, 2015 (21 pages).
The Corrected Notice of Allowability for U.S. Appl. No. 13/361,374 mailed Feb. 11, 2016 (7 pages).
The Final Office Action for U.S. Appl. No. 13/361,388 mailed Sep. 11, 2015 (28 pages).
The Office Action for U.S. Appl. No. 14/474,569 mailed Mar. 21, 2016 (33 pages).

METHOD OF FORMING A CERMET-CONTAINING BUSHING FOR AN IMPLANTABLE MEDICAL DEVICE HAVING A CONNECTING LAYER

CROSS-REFERENCE TO RELATED APPLICATIONS

This application is a divisional of U.S. patent application Ser. No. 13/361,362, entitled "CERMET-CONTAINING BUSHING FOR AN IMPLANTABLE MEDICAL DEVICE HAVING A CONNECTING LAYER," having a filing date of Jan. 30, 2012, which claims the benefit of the filing date of U.S. Provisional Patent Application Ser. No. 61/438,033, filed Jan. 31, 2011, entitled "CERMET-CONTAINING BUSHING FOR AN IMPLANTABLE MEDICAL DEVICE HAVING A CONNECTING LAYER," which claims priority to German Patent Application No. DE 10 2011 009 858.5, filed on Jan. 31, 2011, and all of which are incorporated herein by reference.

This patent application is also related to patent application Ser. No. 13/361,322 filed on Jan. 30, 2012, entitled "CERAMIC BUSHING FOR AN IMPLANTABLE MEDICAL DEVICE"; patent application Ser. No. 13/361,340 filed on Jan. 30, 2012, entitled "DIRECTLY APPLICABLE ELECTRICAL BUSHING"; patent application Ser. No. 13/361,348 filed on Jan. 30, 2012, entitled "IMPLANTABLE DEVICE HAVING AN INTEGRATED CERAMIC BUSHING"; patent application Ser. No. 13/361,355 filed on Jan. 30, 2012, entitled "HEAD PART FOR AN IMPLANTABLE MEDICAL DEVICE"; patent application Ser. No. 13/361,370 filed on Jan. 30, 2012, entitled "ELECTRICAL BUSHING WITH CERMET-CONTAINING CONNECTING ELEMENT FOR AN ACTIVE IMPLANTABLE MEDICAL DEVICE"; patent application Ser. No. 13/361, 374 filed on Jan. 30, 2012, entitled "CERAMIC BUSHING WITH FILTER"; patent application Ser. No. 13/361,383 filed on Jan. 30, 2012, entitled "CERAMIC BUSHING WITH INDUCTIVE FILTER"; patent application Ser. No. 13/361,388 filed on Jan. 30, 2012, entitled "CERAMIC BUSHING HAVING HIGH CONDUCTIVITY CONDUCTING ELEMENTS"; patent application Ser. No. 13/361,398 filed on Jan. 30, 2012, entitled "METHOD FOR THE MANUFACTURE OF A CERMET-CONTAINING BUSHING"; patent application Ser. No. 13/361,404 filed on Jan. 30, 2012, entitled "METHOD FOR THE MANUFACTURE OF A CERMET-CONTAINING BUSHING FOR AN IMPLANTABLE MEDICAL DEVICE"; and patent application Ser. No. 13/361,411 filed on Jan. 30, 2012, entitled "CERMET-CONTAINING BUSHING WITH HOLDING ELEMENT FOR AN IMPLANTABLE MEDICAL DEVICE".

BACKGROUND

One aspect relates to an electrical bushing for use in a housing of an implantable medical device. Moreover, one aspect relates to a method for the manufacture of an electrical bushing for an implantable medical device.

The post-published document, DE 10 2009 035 972, discloses an electrical bushing for an implantable medical device having the features of the preamble of claim 1. Moreover, a use of at least one cermet-comprising conducting element in an electrical bushing for an implantable medical device and a method for the manufacture of an electrical bushing for an implantable medical device are disclosed.

A multitude of electrical bushings for various applications are known, examples including: U.S. Pat. No. 4,678,868, U.S. Pat. No. 7,564,674 B2, US 2008/0119906 A1, U.S. Pat. No. 7,145,076 B2, U.S. Pat. No. 7,561,917, US 2007/0183118 A1, U.S. Pat. No. 7,260,434B1, U.S. Pat. No. 7,761,165, U.S. Pat. No. 7,742,817 B2, U.S. Pat. No. 7,736,191 B1, US 2006/0259093 A1, U.S. Pat. No. 7,274,963 B2, US 2004116976 A1, U.S. Pat. No. 7,794,256, US 2010/0023086 A1, U.S. Pat. No. 7,502,217 B2, U.S. Pat. No. 7,706,124 B2, U.S. Pat. No. 6,999,818 B2, EP 1754511 A2, U.S. Pat. No. 7,035,076, EP 1685874 A1, WO 03/073450 A1, U.S. Pat. No. 7,136,273, U.S. Pat. No. 7,765,005, WO 2008/103166 A1, US 2008/0269831, U.S. Pat. No. 7,174,219 B2, WO 2004/110555 A1, U.S. Pat. No. 7,720,538 B2, WO 2010/091435, US 2010/0258342 A1, US 2001/0013756 A1, U.S. Pat. No. 4,315,054, and EP 0877400.

DE 697 297 19 T2 describes an electrical bushing for an active implantable medical device—also called implantable device or therapeutic device. Electrical bushings of this type serve to establish an electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one of its sides. Said connection body includes a hollow space having at least one connection socket for connecting electrode leads. In this context, the connection socket includes electrical contacts in order to electrically connect the electrode leads to the control electronics on the interior of the housing of the implantable therapeutic device. Hermetic sealing with respect to a surrounding is an essential prerequisite of an electrical bushing of this type. Therefore, lead wires that are introduced into an electrically insulating base body—also called signal-transmission elements—through which the electrical signals are propagated, must be introduced into the base body such as to be free of gaps. In this context, it has proven to be challenging that the lead wires generally are made of a metal and are introduced into a ceramic base body. In order to ensure durable connection between the two elements, the internal surface of a through-opening—also called openings—in the base body is metallized in order to attach the lead wires by soldering. However, the metallization in the through-opening has proven to be difficult to apply. Only cost-intensive procedures ensure homogeneous metallization of the internal surface of the bore hole—and thus a hermetically sealed connection of the lead wires to the base body by soldering. The soldering process itself requires additional components, such as solder rings. Moreover, the process of connecting the lead wires to the previously metallized insulators utilizing the solder rings is a process that is laborious and difficult to automate.

In general, an object of at least on embodiment is to overcome, at least in part, the resulting disadvantages according to the prior art.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the invention are evident from the claims, the description provided hereinafter, and the drawings. The invention is illustrated through several exemplary embodiments in the drawings. In this context, equal or functionally equal or functionally corresponding elements are identified through the same reference numbers. The invention shall not be limited to the exemplary embodiments.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment creates an electrical bushing for an implantable medical device, in which at least some of the disadvantages mentioned above is prevented at least in part.

Another embodiment enables the electrical bushing to be contacted easily. The subject matter of the category-forming claims provides a contribution to the resolution of at least one of features. The sub-claims depending on these claims are refinements of said features. Features and details are described in the context of the electrical bushing or the implantable medical device shall also apply in relation to the method, and vice versa.

In summary, the following embodiments are proposed:

According one embodiment, an electrical bushing for use in a housing of an implantable medical device is proposed, whereby the electrical bushing includes at least one electrically insulating base body and at least one electrical conducting element, whereby the conducting element is set up to establish, through the base body, at least one electrically conducting connection between an internal space of the housing and an external space, whereby the conducting element is hermetically sealed with respect to the base body, whereby the at least one conducting element includes at least one cermet, whereby the at least one conducting element includes at least one electrically conductive connecting layer. In one embodiment, this is provided between the conducting element and a wire-like structure. Moreover, in one embodiment at least 50% by weight, in one embodiment at least 75% by weight, and in one embodiment at least 95% by weight of the connecting layer are situated on the surface of one of the two ends of the conducting element. In one embodiment, no part of the connecting layer is connected to the base body.

The electrically conductive connecting layer in one embodiment not only establishes a firm and mechanically stable connection to the conducting element, but also establishes a simple, but mechanically stable connection to further electrically conductive elements that are to be attached to the conducting element. Since the conducting element itself is in one embodiment made from a cermet, at least in part, and includes to some extent, for example, ceramic integral components, it is not feasible without a major effort to establish a connection to further electrically conductive materials. For this reason, it is advantageous in one embodiment to introduce a connecting layer between the electrical bushing and electrically conductive materials, such as, for example, a wire to be connected to the conduction element, whereby the connecting layer enables an easily provided and firm connection to the conducting element, on the one hand, and, for example, the wire, on the other hand.

In a further embodiment of the electrical bushing, the connecting layer includes a metal. In this context, in one embodiment the connecting layer includes at least 50% by weight, in one embodiment at least 80% by weight, and in one embodiment at least 95% by weight, each relative to the connecting layer, of a metal or a metal alloy. In one embodiment, the metal can be selected from the group consisting of gold (Au), silver (Ag), and platinum (Pt), or two of these. However, other materials that are capable of conducting electrical current and are known to a person skilled in the art are feasible just as well. These can be, for example, other metals or mixtures of metals, such as copper, chromium, nickel, iron or palladium as well as mixtures or alloys thereof.

Moreover, it is feasible that the at least one connecting layer is adjacent to a wire-like structure. In this context, in one embodiment the connecting layer is connected to one or more elements of the electronics unit through the wire-like structure. A wire-like structure can be understood to mean a wire or punched wire structure. According to one embodiment, this is to mean that said wire-like structure is capable of conducting electrical current. In one embodiment, a resistance in the range of 0.1 to 0.5 Ohm*mm$^2$/m should not be exceeded. Moreover, the wire-like structure should enable a connection between the conducting element of the electrical bushing and a further electrical device, such as, for example, another cermet, a battery or any other electrical units. The wire or wire-like structure can be connected through a micro process welding procedure. In the micro process welding procedure, for example, a pressure acts for a limited time of a few minutes to hours onto the interface of wire and connecting layer. Moreover, alternatively or in addition, the process can proceed at elevated temperature, in one embodiment in the range from 180-220° C. Moreover or alternatively, the micro process welding procedure can be carried out by means of ultrasound waves. The wire and conducting element materials thus treated allow wedge- and/or ball-shaped firmly bonded connections to be attained. It is preferable in one embodiment to use wires having a circular cross-section.

The wire-like structure can, for example, be a common wire made of electrically conductive material, such as, for example, copper, iron or other metals or alloys. Alternatively or in addition, the wire-like structure can be a stamped wire structure. In one embodiment, a stamped wire structure is introduced into an object such as, for example, a housing of a device.

In a further embodiment of the electrical bushing, the at least one conducting element includes at least two connecting layers. This can be advantageous in one embodiment, if the electrical bushing is incorporated into a housing, for example of a medical device, and the conducting element is to be connected to electronic elements both inside the housing and outside of the housing. In this case, in one embodiment it is advantageous that the conducting element includes a connecting layer each on the end projecting into the inside of the housing and on the end that is situated outside of the housing.

In one embodiment of the electrical bushing, the base body and the at least one conducting element are connected in a firmly bonded manner, for example, through a firmly bonded sintered connection. According to one embodiment, the term, firmly bonded, shall be understood to mean that the two parts to be connected form a unit after being connected and the connection illustrates itself to be at least as stable as at least one of the two parts. As a result, the connected parts may not fracture at the connecting site when exposed to a mechanical or pressure strain, but rather at a different site of the two connected parts. By this means, it can be ensured that the connection is equally or less porous or gas- or moisture-permeable as/than the parts to be connected.

Moreover, an electrical bushing is proposed, whereby the cermet includes a ceramic component selected from the group consisting of: aluminum oxide, zirconium oxide, zirconium-modified aluminum, aluminum-modified zirconium, Yttrium-toughened zirconium oxide, aluminum nitrite, magnesium oxide, piezoceramic materials and at least two thereof. In one embodiment, the piezoceramic material is lead-free.

In one embodiment of an electrical bushing, the cermet includes a metal component selected from the group consisting of: platinum, platinum alloys, iridium, niobium, molybdenum, tantalum, in one embodiment, tantalum alloys, tungsten, in one embodiment, tungsten alloys or at least two thereof.

Moreover, the base body of an embodiment of the electrical bushing according to one embodiment is selected from the group consisting of: aluminum oxide, zirconium oxide, zirconium-modified aluminum, aluminum-modified zirconium, Yttrium-toughened zirconium oxide, aluminum nitrite, magnesium oxide, piezoceramic materials and at least two thereof. In one embodiment, the piezoceramic material is lead-free.

In a further embodiment of the electrical bushing, the wire-like structure includes a metal component selected from the group consisting of: platinum, in one embodiment platinum alloys, iridium, niobium, molybdenum, tantalum, in one embodiment, tantalum alloys, titanium, in one embodiment, titanium alloys, tungsten, in one embodiment, tungsten alloys, iron, cobalt, chromium, in one embodiment, cobalt-chromium alloys, or at least two thereof. Said materials are particularly well-suited to conduct electrical current very well and, on the other hand, to enter into a stable connection to further metallic components. Moreover, said materials are biocompatible which renders them well-suited for use in implantable devices.

The base body of an electrical bushing according to one embodiment is made from an insulating composition of materials, at least in part. In one embodiment, the insulating composition of materials is selected from the group consisting of: aluminum oxide, magnesium oxide, zirconium oxide, aluminum titanate and piezoceramic materials. As shall be illustrated in more detail below, said materials are particularly well-suited to render the electrical bushing hard enough to be able to withstand mechanical strains, while they are sufficiently biocompatible to be used in implantable devices.

The proposed electrical bushing is set up for use in an implantable medical device, whereby the implantable medical device can be provided, for example, as an active implantable medical device (AIMD) and in one embodiment as a therapeutic device.

As a matter of principle, the term, implantable medical device, shall include any device which is set up to perform at least one medical function and which can be introduced into a body tissue of a human or animal user. As a matter of principle, the medical function can include any function selected from the group consisting of a therapeutic function, a diagnostic function, and a surgical function. For example, the medical function can include at least one actuator function, in which an actuator is used to exert at least one stimulus on the body tissue, for example, an electrical stimulus.

As a matter of principle, the term, active implantable medical device—also called AIMD—shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

The implantable medical device, for example, the active implantable medical device, can usually include, for example, at least one housing, for example, at least one hermetically sealed housing. The housing can in one embodiment enclose at least one electronics unit, for example a triggering and/or analytical electronics unit of the implantable medical device.

In the scope of one embodiment, a housing of an implantable medical device shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element from stresses occurring during operation and/or handling, and/or protection to the functional element from influences of its surroundings such as, for example, influences of a body fluid. The housing can, for example, border and/or close the implantable medical device with respect to the outside.

In this context, an internal space shall be understood herein to mean a region of the implantable medical device, for example, within the housing, which can take up the functional element fully or in part and which, in an implanted state, does not contact the body tissue and/or a body fluid. The internal space can include at least one hollow space which can be closed fully or in part. However, alternatively, the internal space can be filled up fully or in part, for example by the at least one functional element and/or by at least one filling material, for example at least one casting, for example at least one casting material in the form of an epoxy resin or a similar material.

An external space, in contrast, shall be understood to be a region outside of the housing. This can, for example, be a region which, in the implanted state, can contact the body tissue and/or a body fluid. Alternatively or in addition, the external space can just as well be or include a region that is only accessible from outside the housing without necessarily contacting the body tissue and/or the body fluid, for example a region of a connecting element of the implantable medical device that is accessible from outside to an electrical connecting element, for example an electrical plug connector.

The housing and/or, for example, the electrical bushing can, for example, be provided to be hermetically sealed such that, for example, the internal space, is hermetically sealed with respect to the external space. In this context, the term, "hermetically sealed", can illustrate that moisture and/or gases cannot permeate through the hermetically sealed element at all or only to a minimal extent upon intended use for the common periods of time (for example 5-10 years). The leakage rate, which can be determined, for example, by leak tests, is a physical parameter that can described, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of one embodiment, said maximal permissible helium leak rates can, for example, be from $1\times10^{-8}$ atm*cm$^3$/sec to $1\times10^{-7}$ atm*cm$^3$/sec. In the scope of one embodiment, the term, "hermetically sealed", shall be understood, for example, to mean that the device to be tested (for example the housing and/or the electrical bushing and/or the housing with the electrical bushing) has a helium leak rate of less than $1\times10^{-7}$ atm*cm$^3$/sec. In one embodiment, the helium leak rate can be less than $1\times10^{-8}$ atm*cm$^3$/sec, for example, less than $1\times10^{-9}$ atm*cm$^3$/sec. For the purpose of standardization, the above-mentioned helium leak rates can also be converted into the equivalent standard air leak rate. The definition of the equivalent standard air leak rate and the conversion are specified in the ISO 3530 standard.

Electrical bushings are elements set up to create at least one electrically conducting path that extends between the internal space of the housing to at least one external point or region outside the housing, for example, situated in the external space. Accordingly, this establishes, for example, an electrical connection to leads, electrodes, and sensors that are arranged outside the housing.

Common implantable medical devices are commonly provided with a housing, which can include, on one side, a head part, also called header or connecting body, that carries connection sockets for connection of leads, also called electrode leads. The connection sockets include, for example, electrical contacts that serve to electrically connect the leads to a control electronics unit on the interior of the housing of the medical device. Usually, an electrical bushing is provided in the location, at which the electrical connection enters into the housing of the medical device, and the electrical bushing is inserted into a corresponding opening of the housing in a hermetically sealing manner.

Due to the type of use of implantable medical devices, their hermetic sealing and biocompatibility are usually amongst the foremost requirements. The implantable medical device proposed herein according to one embodiment, can be inserted, for example, into a body of a human or animal user, for example, of a patient. As a result, the implantable medical device is usually exposed to a fluid of a body tissue of the body. Accordingly, it is usually important that no body fluid penetrates into the implantable medical device and that no liquids leak from the implantable medical device. In order to ensure this, the housing of the implantable medical device, and thus the electrical bushing as well, should be as impermeable as possible, for example, with respect to body fluids.

Moreover, the electrical bushing should ensure high electrical insulation between the at least one conducting element and the housing and/or the multiple conducting elements provided that more than one conducting element are present. In this context, the insulation resistance reached in one embodiment is at least several MOhm, in one embodiment, more than 20 MOhm, and the leakage currents reached can be small, in one embodiment, less than 10 pA. Moreover, in case multiple conducting elements are present, the crosstalk and electromagnetic coupling between the individual conducting elements in one embodiment are below the specified thresholds for medical applications.

The electrical bushing disclosed according to one embodiment is particularly well-suited for the above-mentioned applications. Moreover, the electrical bushing can also be used in other applications that are associated with special requirements with regard to biocompatibility, tight sealing, and stability.

The electrical bushing according to one embodiment can meet, for example, the above-mentioned tight sealing requirements and/or the above-mentioned insulation requirements.

As mentioned above, the electrical bushing includes at least one electrically insulating base body. In the scope of one embodiment, a base body shall be understood to mean an element that serves a mechanical holding function in the electrical bushing, for example in that the base body holds or carries the at least one conducting element either directly or indirectly. For example, the at least one conducting element can be embedded in the base body directly or indirectly, fully or partly, for example, through a firmly bonded connection between the base body and the conducting element and in one embodiment through co-sintering of the base body and the conducting element. For example, the base body can have at least one side facing the internal space and at least one side facing the external space and/or accessible from the external space.

As mentioned above, the base body is provided to be electrically insulating. This means that the base body, fully or at least regions thereof, is made from at least one electrically insulating material. In this context, an electrically insulating material shall be understood to mean a material with a resistivity of at least $10^7$ Ohm*m, in one embodiment, of at least $10^8$ Ohm*m, in one embodiment of at least $10^9$ Ohm*m, and in one embodiment of at least $10^{11}$ Ohm*m. For example, the base body can be provided such that, as mentioned above, a flow of current between the conducting element and the housing and/or between multiple conducting elements is at least largely prevented, for example through the resistivity values between the conducting element and the housing as specified above being implemented. For example, the base body can include at least one ceramic material.

In this context, a conducting element or electrical conducting element shall generally be understood to mean an element set up to establish an electrical connection between at least two sites and/or at least two elements. For example, the conducting element can include one or more electrical conductors, for example metallic conductors. In the scope of one embodiment, the conducting element is made fully or partly of at least one cermet, as mentioned above. In addition, one or more other electrical conductors, for example metallic conductors, can be provided. The conducting element can, for example, be provided in the form of one or more contact pins and/or curved conductors. Moreover, the conducting element can include, for example, on a side of the base body and/or electrical bushing facing the internal space or on a side of the base body and/or electrical bushing facing the external space or accessible from the external space, one or more connecting contacts, for example one or more plug-in connectors, for example one or more connecting contacts, which project from the base body or can be electrically contacted through other means from the internal space and/or the external space.

The at least one conducting element can establish the electrically conductive connection between the internal space and the external space in a variety of ways. For example, the conducting element can extend from at least one section of the conducting element that is arranged on the side of the base body facing the internal space to at least one section of the conducting element arranged on the side facing the external space or accessible from the external space. However, other arrangements are also feasible as a matter of principle. Accordingly, the conducting element can just as well include a plurality of partial conducting elements that are connected to each other in an electrically conducting manner. Moreover, the conducting element can extend into the internal space and/or the external space. For example, the conducting element can include at least one region that is arranged in the internal space and/or at least one region that is arranged in the external space, whereby the regions can, for example, be electrically connected to each other. Various exemplary embodiments shall be illustrated in more detail below.

The at least one conducting element can include, on a side of the base body and/or electrical bushing facing the internal space or on a side of the base body and/or electrical bushing facing the external space or accessible from the external space, at least one electrical connecting element and/or be connected to an electrical connecting element of this type. For example, as described above, one or more plug-in connectors and/or one or more contact surfaces and/or one or more contact springs and/or one or more types of electrical connecting elements can be provided on one or both of said sides. The at least one optional connecting element can, for example, be a component of the at least one conducting element and/or can be connected to the at least one conducting element in an electrically conducting manner. For example, one or more conducting elements of the bushing can be contacted to one or more internal connecting elements and/or one or more external connecting elements. The material of the internal connecting elements should be suited for permanent connection to the conducting element. The external connecting elements should be biocompatible and should be such that they can be permanently connected to the at least one conducting element.

The electrically insulating base body can support, as a bearing, for example, the at least one conducting element. The at least one material of the base body should be biocompatible in one embodiment, as illustrated above, and should have sufficiently high insulation resistance. It has proven to be advantageous in one embodiment for the base body to include one or more materials selected from the group consisting of: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, and sodium-potassium-niobate.

Moreover, the electrical bushing can also include a holding element that can serve for easy connection of the bushing to a housing, for example, of a medical device. The holding element in one embodiment surrounds the base body, at least in part, and serves as connecting element between base body and housing of the implantable device. The materials of the holding element should be biocompatible, easy to process, corrosion-resistant, and permanently connectable to the base body and the housing in a firmly bonded manner. It has proven to be advantageous for the holding element according to one embodiment to include at least one of the following metals and/or an alloy based on at least one of the following metals: platinum, iridium, niobium, molybdenum, tantalum, tungsten, titanium, cobalt-chromium alloys or zirconium.

In the proposed electrical bushing, the at least one conducting element includes at least one cermet.

The base body can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors.

In the scope of in one embodiment, "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added.

In the scope of one embodiment, sintering or a sintering process shall generally be understood to mean a method for producing materials or work-pieces, in which powdered, for example, fine-grained, ceramic and/or metallic substances are heated and thus connected. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, in one embodiment, at least 100 bar, or even at least 1000 bar. The process can proceed, in one embodiment, fully, or partly at temperatures below the melting temperature of the powdered material, for example at temperatures of 700° C. to 1400° C. The process can be implemented, for example, fully, or partly in a tool and/or a mold such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

A method can be used, for example, in the manufacture of the at least one conducting element and/or optionally in the manufacture of the at least one base body, in which at least one green compact is manufactured first, subsequently at least one brown compact is manufactured from said green compact, and subsequently the finished work-piece is manufactured from said brown compact through at least one sintering step. In this context, separate green compacts and/or separate brown compacts can be manufactured for the conducting element and the base body and can be connected subsequently. Alternatively, one or more common green compacts and/or brown compacts can be produced for the base body and the conducting element. Alternatively again, separate green compacts can be produced first, said green compacts can then be connected, and subsequently a common brown compact can be produced from the connected green compact. In general, a green compact shall be understood to mean a pre-form body of a work-piece which includes the starting material, for example the at least one ceramic and/or metallic powder, as well as, if applicable, the one or more binding agents and/or one or more solvents. A brown compact shall be understood to mean a pre-form body which is generated from the green compact through at least one debinding step, for example at least one thermal and/or chemical debinding step, whereby the at least one binding agent and/or the at least one solvent is/are removed, at least partly, from the pre-form body in the debinding step.

The sintering process, for example, of a cermet, but of the base body just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the bushing according to one embodiment, the at least one ceramic component of the cermet can include, for example, at least one of the following materials: aluminum oxide ($Al_2O_3$), zirconium dioxide ($ZrO_2$), aluminum oxide-toughened zirconium oxide (ZTA), zirconium oxide-toughened aluminum oxide (ZTA—Zirconia Toughened Aluminum—$Al_2O_3/ZrO_2$), yttrium-toughened zirconium oxide (Y-TZP), aluminum nitride (AlN), magnesium oxide (MgO), piezoceramic materials, barium (Zr, Ti) oxide, barium (CE, Ti) oxide, or sodium-potassium-niobate.

For the bushing according to one embodiment, the at least one metallic component of the cermet can include, for example, at least one of the following metals and/or an alloy based on at least one of the following metals: platinum, iridium, niobium, molybdenum, tantalum, tungsten, titanium, cobalt or zirconium. An electrically conductive connection is usually established in the cermet when the metal content exceeds the so-called percolation threshold at which the metal particles in the sintered cermet are connected to each other, at least in spots, such that electrical conduction is enabled. For this purpose, experience tells that the metal content should be 25% by volume and more, in one embodiment 32% by volume, in one embodiment more than 38% by volume, depending on the selection of materials.

In the scope of one embodiment, the terms, "including a cermet," "comprising a cermet," and "cermet-containing", are used synonymously. Accordingly, the terms refer to the property of an element, being that the element contains cermet. This meaning also includes the variant of an embodiment in that elements, for example the conducting element, consist of a cermet, that is, are fully made of a cermet.

In one embodiment, both the at least one conducting element and the base body can include one or more components which are or can be manufactured in a sintering procedure, or the at least one conducting element and the base body are or can both be manufactured in a sintering procedure. For example, the base body and the conducting element are or can be manufactured in a co-sintering procedure, that is, a procedure of simultaneous sintering of these elements. For example, the conducting element and the base body each can include one or more ceramic components that are manufactured, and in one embodiment compacted, in the scope of at least one sintering procedure.

For example, a base body green compact can be manufactured from an insulating composition of materials. This can proceed, for example, by compressing the composition of materials in a mold. In this context, the insulating composition of materials is a powder mass, in which the powder particles illustrate at least minimal cohesion. In this context, the production of a green compact proceeds, for example, through compressing powder masses or through forming followed by drying.

Said procedural steps can also be utilized to form at least one cermet-containing conducting element green compact. In this context, one embodiment can provide that the powder, which is compressed to form the conducting element green compact, is cermet-containing or consists of a cermet or includes at least one starting material for a cermet. Subsequently, the two green compacts—the base body green compact and the conducting element green compact—can be combined. The production of the conducting element green compact and the base body green compact can just as well proceed simultaneously, for example, by multi-component injection molding, co-extrusion, etc., such that there is no longer a need to connect them subsequently.

While the green compacts are being sintered, they are in one embodiment subjected to a heat treatment below the melting temperature of the powder particles of the green compact. This usually leads to compaction of the material and thus to ensuing substantial reduction of the porosity and volume of the green compacts. Accordingly, in one embodiment of the method the base body and the conducting element can be sintered jointly. Accordingly, there is in one embodiment no longer a need to connect the two elements subsequently.

Through the sintering, the conducting element becomes connected to the base body in one embodiment in a positive fit-type and/or non-positive fit-type and/or firmly bonded manner. In one embodiment, this achieves hermetic integration of the conducting element into the base body. In one embodiment, there is no longer a need for subsequent soldering or welding of the conducting element into the base body. Rather, a hermetically sealing connection between the base body and the conducting element is attained through the joint sintering and utilization of a cermet-containing green compact.

One refinement of the method according is characterized in that the sintering includes only partial sintering of the at least one optional base body green compact, whereby said partial sintering can effect and/or include, for example, the debinding step mentioned above. In one embodiment, the green compact is heat-treated in the scope of said partial sintering. This is usually already associated with some shrinkage of the volume of the green compact. However, the volume of the green compact has not yet reached its final state. Rather, another heat treatment is usually needed—a final sintering—in which the green compact(s) is/are shrunk to their final size. In the scope of said variant of an embodiment, the green compact is in one embodiment sintered only partly in order to attain a certain stability to render the green compact easier to handle.

The starting material used for producing at least one conducting element green compact and/or at least one base body green compact can, for example, be a dry powder or include a dry powder, whereby the dry powder is compressed in the dry state into a green compact and illustrates sufficient adhesion to maintain its compressed green compact shape. However, optionally, the starting material can include one or more further components in addition to the at least one powder, for example, as mentioned above, one or more binding agents and/or one or more solvents. Said binding agents and/or solvents, for example organic and/or inorganic binding agents and/or solvents, are generally known to the person skilled in the art, and are commercially available, for example. The starting material can, for example, include one or more slurries or be a slurry. In the scope of one embodiment, a slurry is a suspension of particles of a powder made of one or more materials in a liquid binding agent, and, if applicable, in a water-based or organic binding agent. A slurry has a high viscosity and can easily be shaped into a green compact without the application of high pressure.

In the case of green compacts made from slurries, the sintering process, which is generally carried out below the melting temperature of the ceramic, cermet or metal materials that are used, but in individual cases can also be carried out just above the melting temperature of the lower melting component of a multi-component mixture, this usually being the metal component, leads to the binding agent slowly diffusing from the slurry. Overly rapid heating leads to a rapid increase of the volume of the binding agent by transition to the gas phase and destruction of the green compact or formation of undesired defects in the workpiece.

Thermoplastic and duroplastic polymers, waxes, thermogelling substances and/or surface-active substances, for example, can be used as binding agent—also called binder. In this context, these can be used alone or as binding agent mixtures of multiple components of this type. If individual elements or all elements of the bushing (base body green compact, conducting element green compact, bushing blank) are produced in the scope of an extrusion procedure, the composition of the binding agent should be such that the line of the elements extruded through the nozzle is sufficiently stable in shape for the shape defined by the nozzle to easily be maintained. Suitable binders, also called binding agents, are known to the person skilled in the art.

In contrast, the conducting element according to the prior art usually is a metal wire. A conducting element provided with a cermet, as is in accordance with one embodiment, can be connected easily to the insulation element since it is a ceramic material. Accordingly, green compacts of both the conducting element and the insulation element can be produced and subsequently subjected to a sintering process. The resulting electrical bushing is not only particularly biocompatible and durable, but also possesses good hermetic sealing properties. Thus, no fissures or connecting sites still to be soldered result between the conducting element and the insulation element. Rather, sintering results in the insulation element and the conducting element becoming connected. A variant of an embodiment, therefore provides the at least one conducting element to consist of a cermet. In this variant of an embodiment, the conducting element includes not only components made of cermet, but is fully made of a cermet.

Usually, cermets are characterized by their particularly high toughness and wear resistance. The "cermets" and/or "cermet-containing" substances can, for example, be or include cutting materials related to hard metals which can dispense with tungsten carbide as the hard substance and can be produced, for example, by a powder metallurgical route. A sintering process for cermets and/or the cermet-containing conducting element proceeds, for example, alike a process for homogeneous powders except that, at identical compression force, the metal is usually compacted more strongly than the ceramic material. Compared to sintered hard metals, the cermet-containing conducting element usually illustrates higher resistance to thermal shock and oxidation. As mentioned above, the ceramic components can be, for example, aluminum oxide ($Al_2O_3$) and/or zirconium dioxide ($ZrO_2$), whereas for example, niobium, molybdenum, titanium, cobalt, zirconium, chromium are conceivable as metallic components.

For integration of the electrical bushing into the housing of a cardiac pacemaker, the electrical bushing can include a holding element. Said holding element is in one embodiment arranged about the base body in a collar-like arrangement. The purpose of the holding element is to establish a non-positive fit- and/or positive fit-type connection to the housing. A media-tight connection between the holding element and the housing must be established in the process.

In one embodiment, the electrical bushing includes a holding element that includes a cermet. The cermet-containing holding element can be connected to the housing of the implantable medical device in an easy, durable and hermetically sealed manner. Another embodiment provides the holding element to not only include a cermet, but to consist of a cermet. Moreover, it is conceivable that the conducting element and the holding element are made from the same material. In this variant, the same materials are used for both the conducting element and the holding element. This relates, for example, to a durable, conductive, and biocompatible cermet. Since both the holding element and the conducting element are still to be connected to metallic components, both must include means to be welded or soldered to them. If a cermet is found that meets the pre-requisites specified above, said cermet can be used for both the holding element and the conducting element in order to obtain a particularly inexpensive electrical bushing.

One embodiment includes an insulation element that is formed from an insulating composition of materials. The purpose of the insulation element is to insulate the conducting wire from the holding element and the other objects of the implantable medical device. Electrical signals that are propagated through the conducting wire shall not be attenuated or short-circuited by contacting the housing of the implantable device. In addition, the composition of the insulation element must be biocompatible to allow for implantation in medical applications. For this reason, in one embodiment the insulation element consists of a glass-ceramic or glass-like material. It has been found to be preferred in one embodiment that the insulating composition of materials of the insulation element is at least any one from the group, aluminum oxide ($Al_2O_3$), magnesium oxide (MgO), zirconium oxide ($ZrO_2$), aluminum titanate ($Al_2TiO_5$), and piezoceramic materials. In this context, aluminum oxide features high electrical resistance and low dielectric losses. These properties are supplemented by the additional high thermal resistance and good biocompatibility.

Another refinement of the bushing according to one embodiment is characterized in that the holding element includes at least one flange, whereby the flange, for example, is electrically conductive. The purpose of the flange is to seal the electrical bushing with respect to a housing of the implantable device. The holding element holds the electrical bushing in the implantable device. In the variant of an embodiment described herein, the holding element includes at least one flange on an external side. These flanges form a bearing, which can be engaged by the lids of the implantable medical device, in particularly engaged in a tightly sealing manner. Accordingly, the holding element including the flanges connected to it can have a U- or H-shaped cross-section. Integrating at least one flange into the holding element ensures that the electrical bushing is integrated into the implantable device in a safe, impact-resistant and durable manner. In addition, the flanges can be provided such that the lids of the implantable device are connected clip-like to the holding element in a non-positive fit-type or positive fit-type manner.

Another refinement of the electrical bushing according to one embodiment is characterized in that the at least one flange includes a cermet. In the scope of said variant of an embodiment, both the holding element and the flange include a cermet. In one embodiment, both the flange and the holding element are made of the same material. By providing the flange as a cermet, the flange can be sintered easily and inexpensively as part of the holding element jointly with the insulation element and the conducting element in the scope of the method to be described below.

The scope of one embodiment also includes an implantable medical device, for example, a cardiac pacemaker or defibrillator, having an electrical bushing according to at least one of the preceding claims and embodiments. Features and details that were described in the context of the electrical bushing and/or the method shall obviously also apply in relation to the implantable medical device.

Features and details that are described in the context of the electrical bushing shall obviously also apply in relation to the method according to various embodiments, and vice versa.

Moreover, one embodiment also relates to a method for the manufacture of an electrical bushing for an implantable medical device. According to in one embodiment, the method for the manufacture of an electrical bushing for an implantable medical device includes the following steps:

A method for the manufacture of an electrical bushing for an implantable medical device proposes that the method includes the following steps:
  a. generating at least one base body green compact for at least one base body from an insulating composition of materials;
  b. forming at least one cermet-containing conducting element green compact for at least one conducting element;
  c. introducing the at least one conducting element green compact into the base body green compact;
  d. subjecting the insulation element green compact with the at least one base body green compact to firing in order to obtain at least one base body with at least one conducting element;
  and applying a connecting layer onto at least one conducting element.

As described above for the electrical bushing, the connecting layer in one embodiment serves to allow for easy connection of the electrical bushing to a further electrical component. The connecting layer can be fabricated from any material that is known to the person skilled in the art to establish an electrically conductive connection between two bodies. For this reason, the connecting layer in one embodiment consists of a metal. In this context, metals, mixtures or alloys that are selected, at least in part, from the group consisting of gold, silver, and platinum, and at least two thereof, are preferred in one embodiment.

In one embodiment, step a) of the method includes a partial sintering of the base body green compact.

Moreover, step b) of the method can include a partial sintering of the conducting element green compact.

In one embodiment, the connecting layer 70 is applied by printing, electroplating, microdosing or a vaporization process. The application of the connecting layer 70, can be effected, for example, through a cathode sputtering process. In this process, bombardment of a solid with energy-rich ions releases atoms which are subsequently deposited in the form of a layer on the substrate, which is the conducting element 30 in the present case. In one embodiment, this process proceeds in a pressure range from $1*10-3$ hPa to $9*10-2$ hPa and at a temperature between 25° C. and 250° C. It can be advantageous in one embodiment to have a bonding agent layer 71 between the substrate, that is, the conducting element 30 in the present case, and the connecting layer 70. Said bonding agent layer 71 can, for example, be selected, at least in part, from the group of chromium, titanium, tantalum, zirconium or two thereof. Said bonding agent layer 71 can be applied, for example, through physical vapor deposition. Alternatively, the connecting layer 70 can be applied through an electroplating process, printing processes such as dabber printing or screen printing as well as through micro-dosing, for example through piezo- or pneumatic valves. If the connecting layer 70 is applied through a printing procedure, it is feasible to use, for example, a printing paste that contains at least one conductive material. Said printing paste often contains, in addition, one or more organic binding agents such as alkyl cellulose (most often methyl cellulose).

Another special feature of the method according to one embodiment results from both the insulation element and the conducting element comprising ceramic components that are processed in the scope of a sintering process. In the scope of step a), an insulation element green compact is generated from an insulating composition of materials. This can be done by compressing the composition of materials in a mold. In this context, the insulating composition of materials is a powder mass, in which the powder particles illustrate at least minimal cohesion. Usually, this is effected in that a grain size of the powder particles does not exceed 0.5 mm.

In this context, the manufacture of the green compact proceeds either by compressing powder masses or by forming and subsequent drying. Said procedural steps are also utilized to form the cermet-containing conducting element green compact. In this context, one embodiment provides the powder, which is compressed into the conducting element green compact, to be cermet-containing or to consist of a cermet. Subsequently, the two green compacts—the insulation element green compact and the conducting element green compact—are combined. After this step, which is called step c), the two green compacts are subjected to firing—which is also called sintering. In the process, the green compacts are subjected to a heat treatment below the melting temperature of the powder particles of the green compact. This leads to a substantial reduction of the porosity and volume of the green compacts. The special feature of the method thus is that the insulation element and the conducting element are jointly subjected to firing. There is no longer a need to connect the two elements after this step. Through the firing process, the conducting element becomes connected to the insulation element in a positive fit-type and/or non-positive fit-type and/or firmly bonded manner. This achieves hermetic integration of the conducting element into the insulation element. There is no longer a need for subsequent soldering or welding of the conducting element into the insulation element. Rather, through the joint firing and the utilization of a cermet-containing green compact, a hermetically sealing connection between the insulation element and the conducting element is attained.

One refinement of the method is characterized in that step a) includes a partial sintering of the insulation element green compact. The green compact of the insulation element is heat-treated in the scope of said partial sintering. This is already associated with some shrinkage of the volume of the insulation element green compact. However, the volume of the green compact does not reach its final state. Rather, this requires another heat treatment in the scope of step d), in which the insulation element green compact and the conducting element green compact are shrunk to their final size. In the scope of said variant of an embodiment, the green compact is heat treated only partly in order to already attain a certain surface hardness to render the insulation element green compact easier to handle. This is expedient for example, in the case of insulating compositions of materials which can be compressed into a green compact shape only with some difficulty.

Moreover, one embodiment relates to a method for treating, in one embodiment, a heart disease of a mammal, in one embodiment a human, comprising the steps:
  i. providing an implantable medical device;
  ii. introducing the implantable medical device into the mammal;
  iii. generating a functional connection between implantable medical device and mammal.

The step of providing the implantable medical device is in one embodiment effected through the method according to one embodiment. Aside from humans, other mammals are conceivable as well, such as animals like dogs, cats, horses, pigs, cows, sheep and goats. The step of introducing the device is in one embodiment effected through a surgical intervention, in which the implantable medical device is inserted into the mammal body by opening the body, and in one embodiment is anchored therein. The functional connection is in one embodiment provided as an electrical connection in order to stimulate a muscle through suitable signals.

Figure 1:
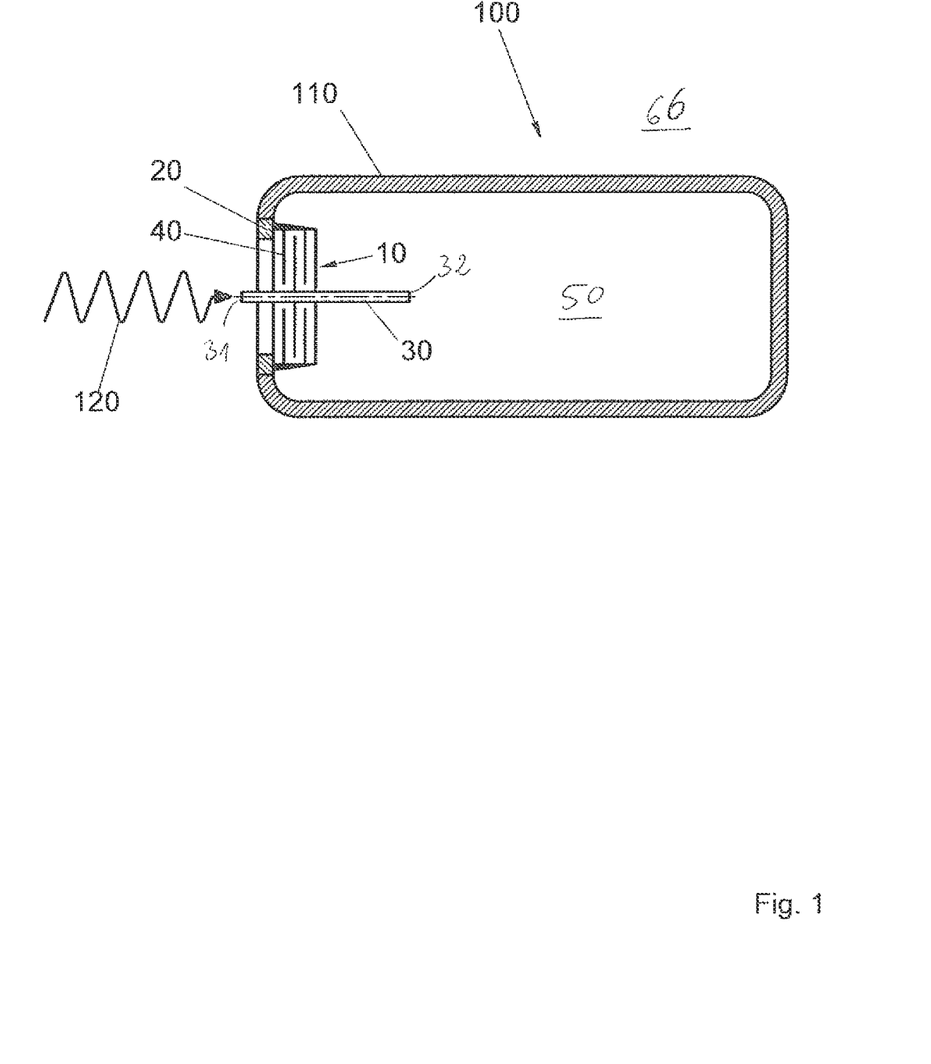
FIG. 1 illustrates an implantable medical device.

FIG. 1 illustrates for exemplary purposes an implantable device 100, such as, for example, a cardiac pacemaker, that has an electrical bushing 10 integrated into its metallic housing. The electrical bushing 10 is connected to the housing 110 of the implantable device 100 in a hermetically sealed manner, for example, through welding. It is therefore advantageous in one embodiment that a holding element 20 of the electrical bushing 10 includes a metal that can be welded to the housing 110 easily and reliably. The purpose of the electrical bushing 10 is to establish an electrical connection between the hermetically sealed interior of the medical device 100 and the exterior. Accordingly, a conducting coil 120, which is only indicated schematically here and is connected to a stimulation electrode, can be connected to the electrical bushing 10. Stimulation electrodes of this type are inserted, for example, in heart muscles to allow signals of the cardiac pacemaker to be conducted to the muscle. In order to attain hermetic sealing, the conducting wire 30 is embedded in an insulation element 40. The insulation element 40 leads to the formation of a hermetic seal between the holding element 20 and the at least one conducting wire 30 in a through opening 22 formed by the collar-like holding element 20. The electrically insulating insulation element prevents electrical short-circuiting to occur between the electrically conductive elongated conducting wire 30 and the metallic housing 110 and/or the metallic holding element 20.

Figure 2:
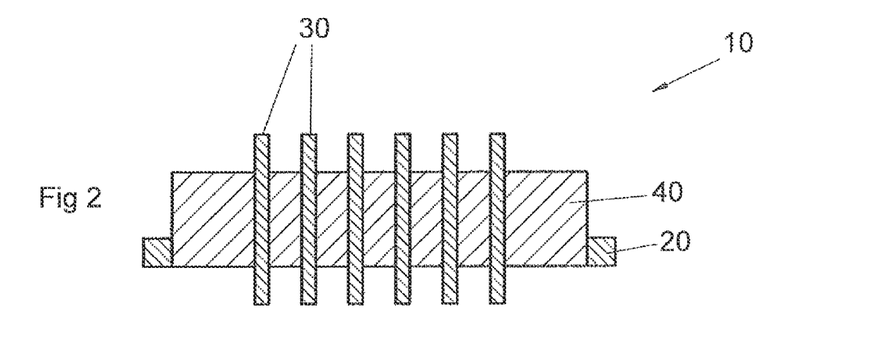
FIG. 2 illustrates a sectional drawing through an electrical bushing according to one embodiment.

In electrical bushings according to the prior art, a metallic wire is used as conducting element and needs to be soldered into an insulation element. For this purpose, the insulation element includes a cylinder-like bushing for the conducting element, with the internal wall of said bushing being provided with a metallic coating. The soldering has proven to be error-prone and expensive. FIG. 2 illustrates an electrical bushing 10 according to in one embodiment that overcomes at least some of the disadvantages mentioned above. The electrical bushing 10 includes a collar-like holding element 20. The holding element 20 serves to hold the electrical bushing 10 in the implantable medical device 100. The holding element 20, designed to be collar-like, includes a through-opening 22. This is particularly evident from FIG. 3, which illustrates a top view onto the electrical bushing 10 illustrated in a section in FIG. 2. Designed rectangular in shape and collar-like, the holding element 20 possesses, on its interior, the through-opening 22, which is designed to be rectangular in the present case. At least one elongated conducting element 30 extends through said through-opening 22. In the exemplary embodiment illustrated, a total of five conducting elements 30 extend through the holding element 20. An insulation element 40 is arranged in the through-opening 22 in such a manner that hermetic sealing is effected between the holding element 20 and the conducting element 30. The special feature according to one embodiment of the electrical bushing 10 illustrated results from the conducting element 30 comprising a cermet or consisting of a cermet.

Figure 3:
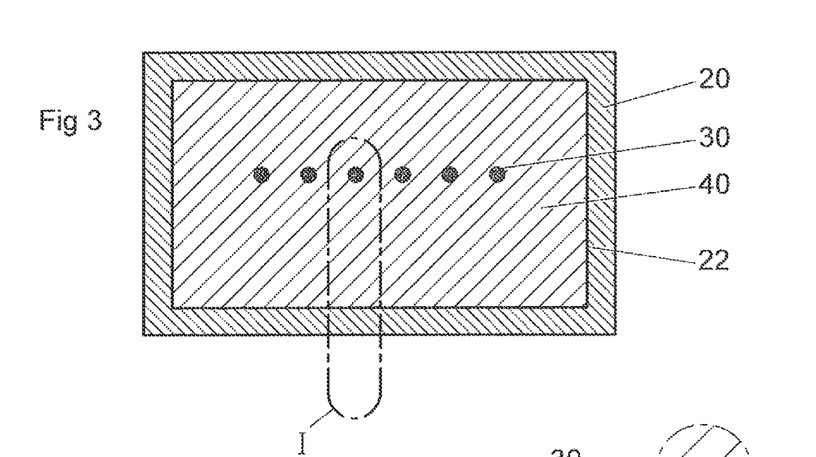
FIG. 3 illustrates a schematic top view onto the electrical bushing according to FIG. 2.

A cermet is a composite material made of ceramic materials in a metallic matrix. The special feature of a cermet-containing conducting element 50 of this type is that it can be sintered jointly with the insulation element 40, which also contains a ceramic material, in a single procedural step. Thus, no undesirable through-openings, fissures or imperfections arise any longer between conducting element 50 and insulation element 40. Rather, a media-tight connection is created between the two elements 40,50. The individual procedural steps for the manufacture of the electrical bushing 10 according to one embodiment are as follows:
  a. generating an insulation element green compact for an insulation element 40 from an insulating composition of materials;
  b. forming at least one cermet-containing conducting element green compact for a conducting element 30;
  c. introducing the at least one conducting element green compact into the insulation element green compact;
  d. connecting the insulation element green compact to the at least one conducting element green compact in order to obtain an insulation element 40 having at least one conducting element 30.

The special feature according to the scope of the method according to one embodiment results from both the insulation element green compact and the conducting element green compact each being compressed from powders and then subjected to firing. Accordingly, in just a few procedural steps a green compact can be generated that includes both the conducting element green compact and the insulation element green compact, and said total green compact is then subjected to firing. In a variant of an embodiment, not only the insulation element 40 and the conducting element 30, but also the holding element 20 are pressed and sintered from powders. Subsequently, the three green compacts—holding element 20, conducting element 30, insulation element 40—are combined. This results in the electrical bushing 10 in a green compact stage. Subsequently, the green compacts are jointly subjected to firing. The resulting electrical bushing 10 not only meets all necessary electrical requirements, but it also is produced in one step without any need for subsequent soldering or welding of individual elements. Moreover, the metal-containing, a cermet containing holding element 20 enables a simple durable connection to the housing of the implantable medical device 100 to be established.

Figure 4:
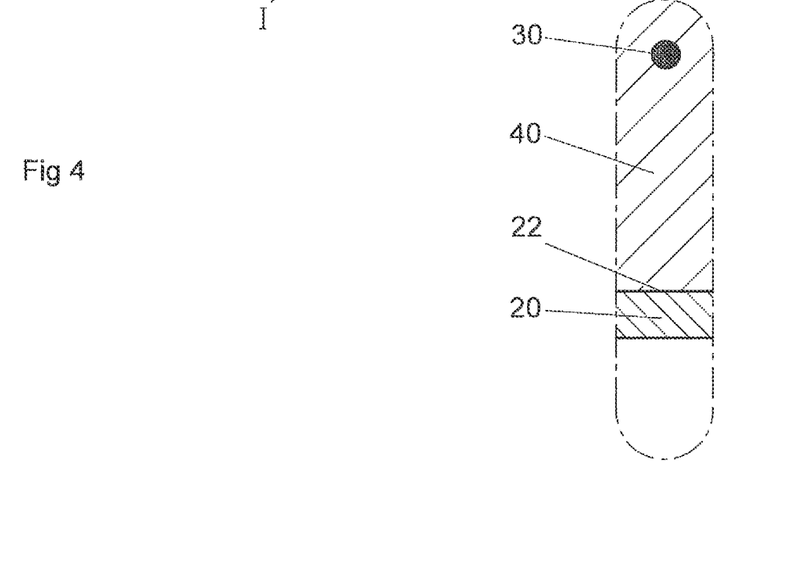
FIG. 4 illustrates a magnified detail of the electrical bushing.

FIG. 4 again illustrates a magnification of the individual components of the electrical bushing 10. This magnified detail corresponds to the region denoted I in FIG. 3. The insulation element 40 that is made from an electrically insulating composition of materials surrounds the conducting element 30. Conducting coils, for example for a cardiac pacemaker, can be connected to said conducting element 30. The insulation element 40 is surrounded by a holding element 20 that is designed to be collar-like in shape. Said holding element 20 is cermet-containing in the variant of the embodiment illustrated. Consequently, the holding element can be subjected to firing or sintering jointly with the cermet-containing bearing element 50 and the electrically insulating insulation element 40 in one step. In one embodiment, the holding element 20 and the bearing element 50 are made of the same material in this context.

For integration of the electrical bushing 10 into the implantable medical device 100, the holding element 20 can include a flange. A flange of this type has not been sketched-in in the figures. A housing 110 of the device 100 can touch against the flange in order to enable a hermetically sealing connection of the two elements. In one embodiment, the holding element 20 and the flange are made of the same material and/or as a single part.

Figure 5:
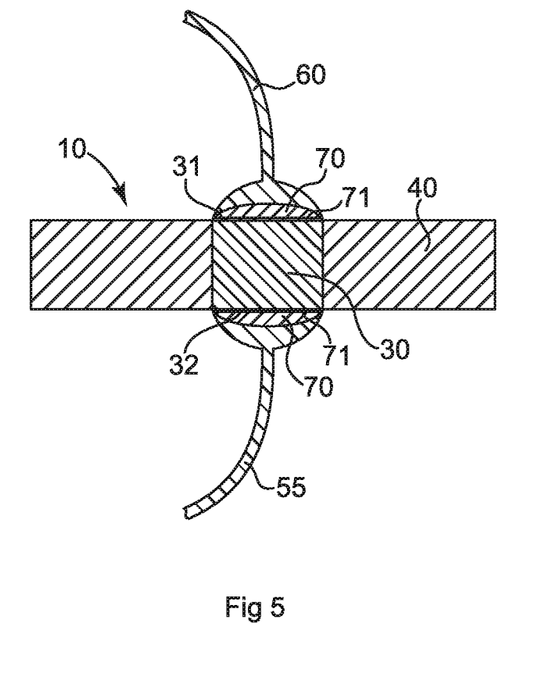
FIG. 5 illustrates a schematic view of an electrical bushing with conducting element connected to wires through a connecting layer.

FIG. 5 illustrates an electrical bushing 10 consisting of a base body 40 with an introduced conducting element 30, which includes a connecting layer 70 each at least at the two ends 31 and 32 of the conducting element 30. Said connecting layer 70 was applied to the conducting element 30 through a cathode sputtering process. This in one embodiment applies a gold (Au) layer with a thickness in the range from 0.1 µm to 5 µm and in one embodiment in a range from 0.2 to 4 µm. Said layer 70 is connected to the conducting element 30 in a particularly durable manner and thus provides a good foundation for further contacting of the conducting element 30 to further electrical elements, such as, for example, a wire 55, 60. The wires 55, 60 illustrated here were applied to the connecting layer 70 through a micro process welding procedure such as bonding or laser welding. The electrical bushing 10 can just as well be connected to a housing 110 of a medical device 100 through a holding element 20, such as is illustrated in FIGS. 1 to 4. By this means, the internal wire 55 points towards the internal space 50 of the device 100 and the wire 60 points towards the external space 66 of the device 100, as illustrated in FIG. 1. By this means, flexible, yet simple contacting of the electrical bushing in both directions, towards the inside 50 and the outside 66 of the device 100, can be effected.

A medical device 100 can be in the form of a cardiac pacemaker that can be implanted into a mammal. The implanted cardiac pacemaker is situated in the immediate vicinity of the heart of the mammal and is implanted under the skin of the mammal. The functional connection between the heart and the cardiac pacemaker is implemented through a wire in most cases. The wire is coupled to the electrical bushing 10 and thus enables the functional connection between the heart and the cardiac pacemaker.

There are procedural steps of the implantation procedure. In the provision step 1110, an implantable device 100 is provided to the user. The implantable device 100 is a cardiac pacemaker in the case of the implant example. In the introduction step, the medical device 100, being cardiac pacemaker in this case, is introduced into the mammal. This can be done through implantation aids which are known adequately according to the prior art regarding cardiac pacemakers. In the connection step, a functional connection between the heart of the user and the cardiac pacemaker is established through the electrical bushing element 10.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method for the manufacture of an electrical bushing for an implantable medical device, the method comprising:
   a. generating at least one base body green compact for at least one base body from an insulating composition of materials;
   b. forming at least one cermet-containing conducting element green compact for at least one conducting element;
   c. introducing the at least one conducting element green compact into the base body green compact;
   d. subjecting the at least one base body green compact and at least one conducting element green body compact to firing in order to obtain at least one base body having at least one conducting element;
   e. applying a connecting layer onto the at least one conducting element, the connecting layer applied in a thickness range between 0.1 µm to 5 µm to provide good foundation for further contacts.

2. The method according to claim 1, whereby the connecting layer is made from a metal.

3. The method according to claim 2, whereby the metal is selected from a group consisting of gold, silver, and platinum.

4. The method according to claim 2, whereby the metal comprises two metals selected from a group consisting of gold, silver, and platinum.

5. The method according to claim 1, whereby step a) comprises a partial sintering of the base body green compact.

6. The method according to claim 1, whereby step b) comprises a partial sintering of the conducting element green compact.

7. The method according to claim 1, whereby the connecting layer is applied by printing, electroplating, micro-dosing or through a vaporization process or a combination thereof.

8. The method according to claim 1 further comprising forming a bonding agent layer between the conducting element and the connecting layer.

9. The method according to claim 8, wherein the bonding agent layer comprises at least one from a group comprising chromium, titanium, tantalum, and zirconium.

10. The method according to claim 1, further comprising forming an electrical bushing from the at least one base body having the at least one conducting element.

11. The method according to claim 1, further comprising attaching a wire-like structure adjacent to the at least one connecting layer.

12. The method according to claim 1, further comprising forming at least one base body brown compact from the at least one base body green compact.

13. The method according to claim 1, further comprising forming at least one cermet-containing conducting element brown compact from the at least one cermet-containing conducting element green compact.

14. The method according to claim 1, further comprising forming the electrical bushing using at least one of a base body brown compact and a cermet-containing conducting element brown compact.

15. A method for the manufacture of an electrical bushing for an implantable medical device, the method comprising:
generating at least one base body green compact for at least one base body from an insulating composition of materials;
forming at least one cermet-containing conducting element green compact for at least one conducting element;
introducing the at least one conducting element green compact into the base body green compact;
subjecting the at least one base body green compact to the at least one base body green compact and at least one conducting element green body compact to firing in order to obtain at least one base body having at least one conducting element;
applying a connecting layer onto the at least one conducting element; and
forming a bonding agent layer between the conducting element and the connecting layer.

16. The method of claim 15, wherein the connecting layer comprises gold and is applied to the conducting element through a cathode sputtering process.

17. The method of claim 16, wherein the cathode sputtering process proceeds in a pressure range from $1*10^{-3}$ hPa to $9*10^{-2}$ hPa and at a temperature between 25° C. and 250° C.

* * * * *